US008663279B2

(12) United States Patent
Burkhart et al.

(10) Patent No.: US 8,663,279 B2
(45) Date of Patent: *Mar. 4, 2014

(54) SWIVEL ANCHOR FOR KNOTLESS FIXATION OF TISSUE

(75) Inventors: Stephen S. Burkhart, San Antonio, TX (US); Peter J. Dreyfuss, Naples, FL (US); John A. Sodeika, Naples, FL (US)

(73) Assignee: Arthrex, Inc., Naples, FL (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/403,402

(22) Filed: Feb. 23, 2012

(65) Prior Publication Data

US 2012/0150226 A1 Jun. 14, 2012

Related U.S. Application Data

(63) Continuation of application No. 12/043,008, filed on Mar. 5, 2008, now abandoned, which is a continuation-in-part of application No. 11/802,507, filed on May 18, 2007.

(60) Provisional application No. 60/801,097, filed on May 18, 2006.

(51) Int. Cl.
*A61B 17/04* (2006.01)

(52) U.S. Cl.
USPC ........................................................ 606/232

(58) Field of Classification Search
None
See application file for complete search history.

(56) References Cited

U.S. PATENT DOCUMENTS

| 4,484,570 | A |   | 11/1984 | Sutter et al. |
| 5,084,050 | A |   | 1/1992  | Draenert |
| 5,129,904 | A |   | 7/1992  | Illi |
| 5,152,790 | A | * | 10/1992 | Rosenberg et al. ........ 623/13.14 |
| 5,860,973 | A |   | 1/1999  | Michelson |
| 5,968,047 | A |   | 10/1999 | Reed |
| 6,143,017 | A |   | 11/2000 | Thal |
| 6,355,043 | B1 |   | 3/2002  | Adam |
| 6,517,542 | B1 |   | 2/2003  | Papay et al. |
| 6,544,281 | B2 |   | 4/2003  | ElAttrache et al. |
| 6,863,671 | B1 |   | 3/2005  | Strobel et al. |
| 7,083,647 | B1 |   | 8/2006  | Sklar et al. |
| 7,261,716 | B2 |   | 8/2007  | Strobel et al. |
| 7,300,439 | B2 |   | 11/2007 | May |
| 7,329,272 | B2 | * | 2/2008  | Burkhart et al. .............. 606/232 |
| 7,585,311 | B2 |   | 9/2009  | Green et al. |
| 7,645,293 | B2 | * | 1/2010  | Martinek et al. ............. 606/232 |
| 7,803,173 | B2 | * | 9/2010  | Burkhart et al. ............. 606/232 |
| 7,981,140 | B2 | * | 7/2011  | Burkhart ...................... 606/232 |
| 7,993,369 | B2 | * | 8/2011  | Dreyfuss ....................... 606/232 |
| 8,012,174 | B2 | * | 9/2011  | ElAttrache et al. ........... 606/232 |
| 2004/0093030 | A1 |   | 5/2004  | Cox et al. |
| 2004/0093031 | A1 | * | 5/2004  | Burkhart et al. ............. 606/232 |
| 2004/0193217 | A1 | * | 9/2004  | Lubbers et al. .............. 606/232 |
| 2005/0119698 | A1 |   | 6/2005  | Martinek |

(Continued)

*Primary Examiner* — Melanie Tyson
*Assistant Examiner* — Todd J Scherbel
(74) *Attorney, Agent, or Firm* — Dickstein Shapiro LLP

(57) ABSTRACT

A method and device for knotless fixation of tissue. A swivel anchor having a rotatable implant is used to capture suture for surgical tissue repair without requiring suture knots. The implant may be provided with a conical metal tip which is self-punching and avoids the need for pre-drilling a hole in bone. The implant includes a closed aperture to allow free sliding of a suture strand. The swivel anchor is secured in a hole in bone by advancing a fixation device, such as a cannulated interference screw, over the body of the implant.

7 Claims, 10 Drawing Sheets

(56) References Cited

U.S. PATENT DOCUMENTS

| | | |
|---|---|---|
| 2006/0004364 A1 | 1/2006 | Green et al. |
| 2006/0100630 A1* | 5/2006 | West, Jr. .................. 606/73 |
| 2006/0235413 A1* | 10/2006 | Denham et al. ............ 606/72 |
| 2006/0247642 A1 | 11/2006 | Stone et al. |
| 2006/0259076 A1* | 11/2006 | Burkhart et al. ........... 606/228 |
| 2007/0038221 A1 | 2/2007 | Fine et al. |
| 2007/0060922 A1 | 3/2007 | Dreyfuss |
| 2007/0135843 A1* | 6/2007 | Burkhart .................... 606/232 |
| 2007/0191849 A1* | 8/2007 | ElAttrache et al. ......... 606/72 |
| 2008/0027444 A1 | 1/2008 | Malek |
| 2008/0154314 A1 | 6/2008 | McDevitt |
| 2008/0215091 A1* | 9/2008 | Dreyfuss .................... 606/232 |
| 2008/0275431 A1* | 11/2008 | Stone et al. ............... 606/1 |
| 2008/0281325 A1 | 11/2008 | Stone et al. |
| 2011/0276092 A1* | 11/2011 | Dreyfuss .................... 606/232 |
| 2011/0313455 A1* | 12/2011 | ElAttrache et al. ......... 606/232 |
| 2012/0150225 A1* | 6/2012 | Burkhart et al. ........... 606/232 |
| 2012/0165868 A1* | 6/2012 | Burkhart et al. ........... 606/232 |

\* cited by examiner

SWIVEL ANCHOR FOR KNOTLESS FIXATION OF TISSUE

This application is a continuation of U.S. application Ser. No. 12/043,008, filed on Mar. 5, 2008, now abandoned, which is a continuation-in-part of U.S. application Ser. No. 11/802, 057, filed on May 18, 2007, which claims the benefit of U.S. Provisional Application Ser. No. 60/801,097, filed on May 18, 2006, the entire disclosures of which are incorporated herein by reference.

FIELD OF THE INVENTION

The present invention relates to methods and instruments for fixation of sutures and tissue to bone.

BACKGROUND OF THE INVENTION

When soft tissue tears away from bone, reattachment becomes necessary. Various devices, including sutures, screws, staples, wedges, anchors and plugs have been used in the prior art to secure soft tissue to bone. Surgical methods utilizing suture anchors alone are disadvantageous for reattachment of large areas of detached tissue because they often do not allow good tissue to bone contact.

Reattachment of soft tissue to bone typically requires the surgeon to pass suture material through selected tissue, form a plurality of surgical knots extracorporeally and then move the knots into position adjacent the desired tissue to be sutured. In such procedures, the surgeon must manually tie the knots on the suture strands after the suture is threaded through the selected tissues to be sutured. Knot tying during surgery, particularly arthroscopic surgery, is tedious and time-consuming. There is also a tendency for the knots to deform or collapse as the surgeon manually forces the knots down into the proper position. Also, the suture knots often are exposed to abrasion or cutting by sharp or rough areas along the walls of the bone canal into which anchors are typically inserted to provide fixation of tendon to bone.

Accordingly, a need exists for an improved method for attaching soft tissue to bone which does not require multiple suture knots and which allows the tendon to remain securely in place until the ligaments naturally attach to bone.

SUMMARY OF THE INVENTION

The instruments and methods of the present invention overcome the disadvantages of the prior art, such as those noted above, by providing a swivel implant at the distal end of a driver that securely engages and locks into a cannulated ribbed body of an interference plug or screw. The swivel implant includes a closed aperture for receiving a strand attached to a graft, such that the strand is able to freely slide through the aperture.

In one embodiment of the invention, the strand is passed through the graft at desired points. A cannulated plug or screw is pre-loaded onto a driver provided with a swivel lock twist-in anchor at its distal end. The strand attached to the graft is passed through the aperture of the swivel implant located at the distal end of the driver. The distal end of the driver together with the implant is inserted directly into the bone. The driver may be rotated (in a clockwise direction, for example) to advance a screw over the anchor to complete insertion.

Other features and advantages of the present invention will become apparent from the following description of exemplary embodiments of the invention described with reference to the accompanying drawings.

DETAILED DESCRIPTION OF THE PREFERRED EMBODIMENTS

The present invention provides apparatus and methods for knotless tissue fixation using a swivel anchor device.

Figure 1:
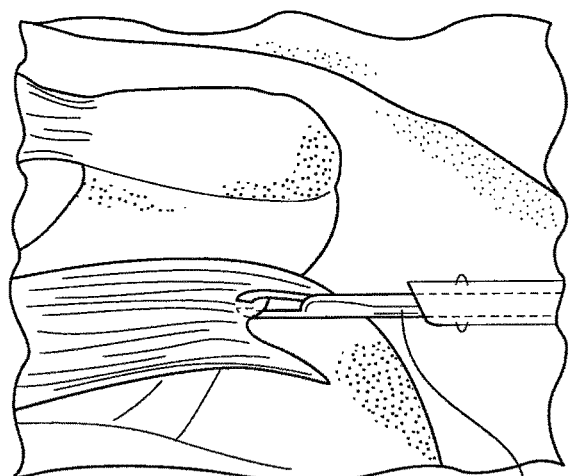
FIGS. 1-6 depict a series of steps of shoulder repair using a plurality of swivel anchor devices according to the present invention.

FIG. 1 illustrates a side view of a human shoulder of a patient undergoing a rotator cuff repair in accordance with an exemplary embodiment of the present invention. The patient may be positioned in the beach chair position using the Arthrex Beach Chair Lateral Traction Device or in a lateral decubitus position using the Arthrex 3-Point Shoulder Distraction System. Access to the subacromial space is facilitated with a variety of cannulas.

First, and as illustrated in FIG. 1, the mobility of the tear is assessed using, for example, a tissue grasper 10 such as the Arthrex KingFisher™ Suture Retriever/Tissue Grasper, to determine whether a U or L-shaped component exists. Where large tears extend to the superior aspect of the glenoid, margin convergence suturing is performed to reduce volume and strain on the repair. Subsequently, the length and width of the rotator cuff footprint is assessed and a bleeding bed for enhanced tendon to bone healing may be formed. This may be accomplished with a burr to perform a light dusting of the greater tuberosity, or by using a chondro pick to microfracture the footprint and maximize vascular channels.

Figure 2:
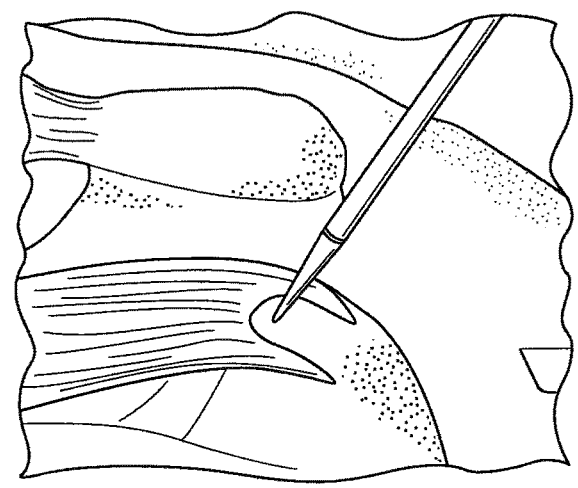

FIG. 2 illustrates the preparation of two pilot holes for two swivel anchors that will be inserted in the medial row. A punch may be employed adjacent to the articular margin of the humerus and at about 45° angle to form the two pilot holes.

Figure 3:
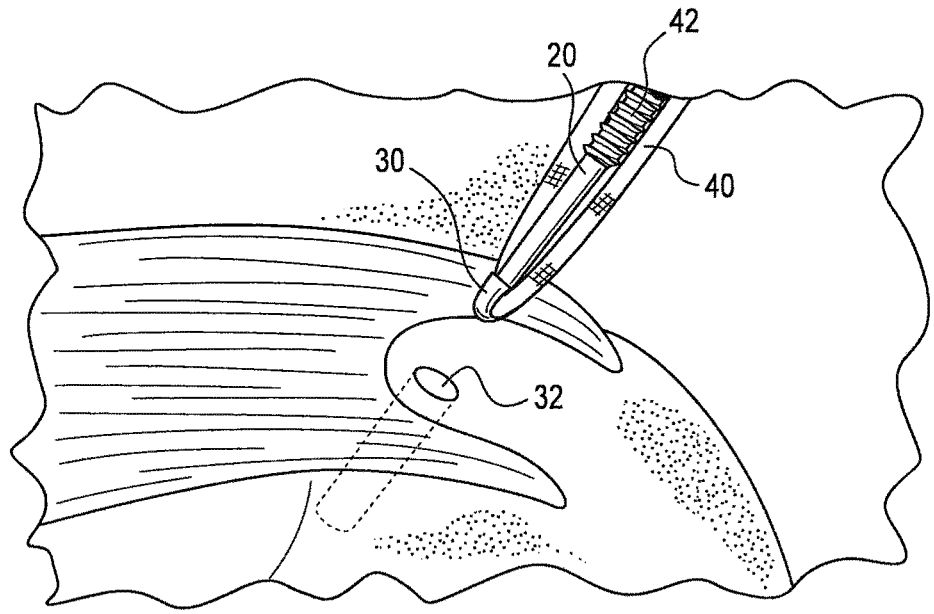
Figure 4:
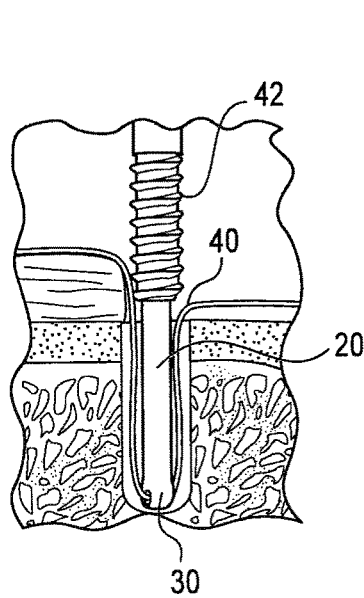
Figure 4A:
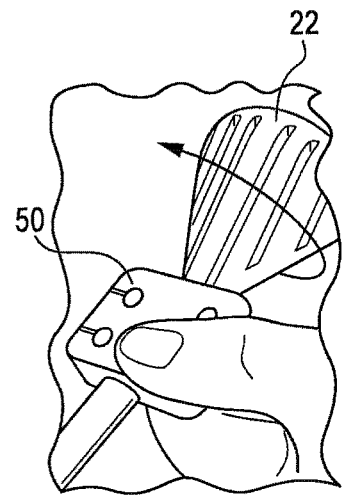

Subsequent to the formation of the pilot holes, and as shown in FIGS. 3 and 4, a swivel implant 30, loaded with a strand of suture tape 40, preferably Arthrex FiberTape, is placed in the medial pre-formed hole 32. Arthrex FiberTape is a high strength suture tape which is braided and rectangular-like in cross section and is disclosed in U.S. Pat. No. 7,892, 256, the disclosure of which is incorporated by reference herein. However, the anchor of the present invention can be used with any type of flexible material or suture. The driver is then rotated to advance screw 42 down shaft 20 to secure the implant and suture in the bone hole. More specifically, as shown in FIG. 4a, the screw 42 is advanced by holding thumb pad 50 as the driver handle 22 is turned clockwise. An Arthrex FiberLink and an Arthrex Scorpion suture passer 44, are used to shuttle both tails of the suture tape through the rotator cuff 34 simultaneously. This procedure is followed for both medial swivel anchors.

Figure 5:
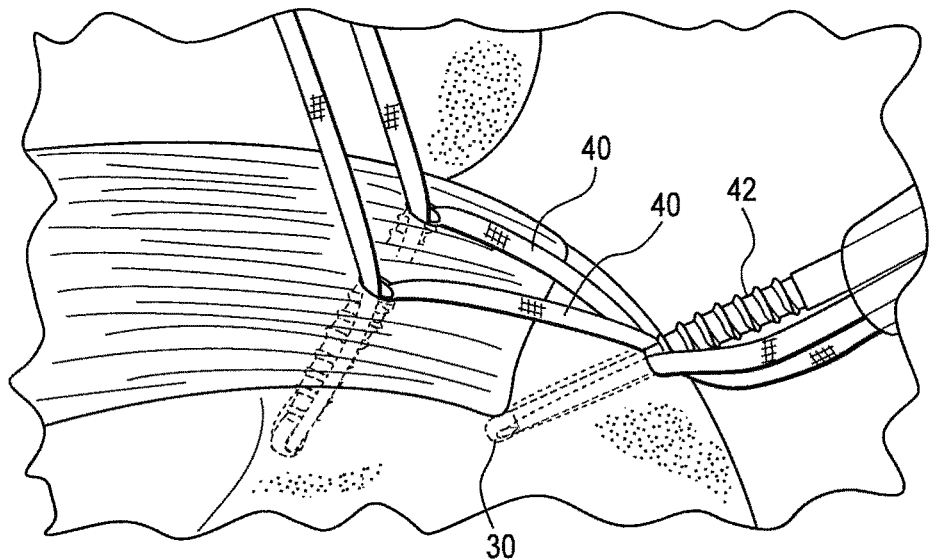
Figure 6:
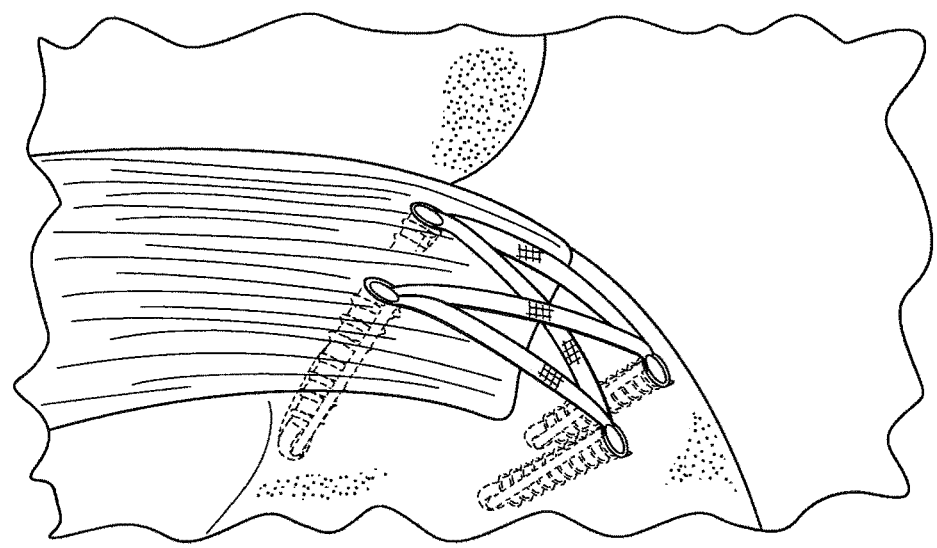
Figure 12:
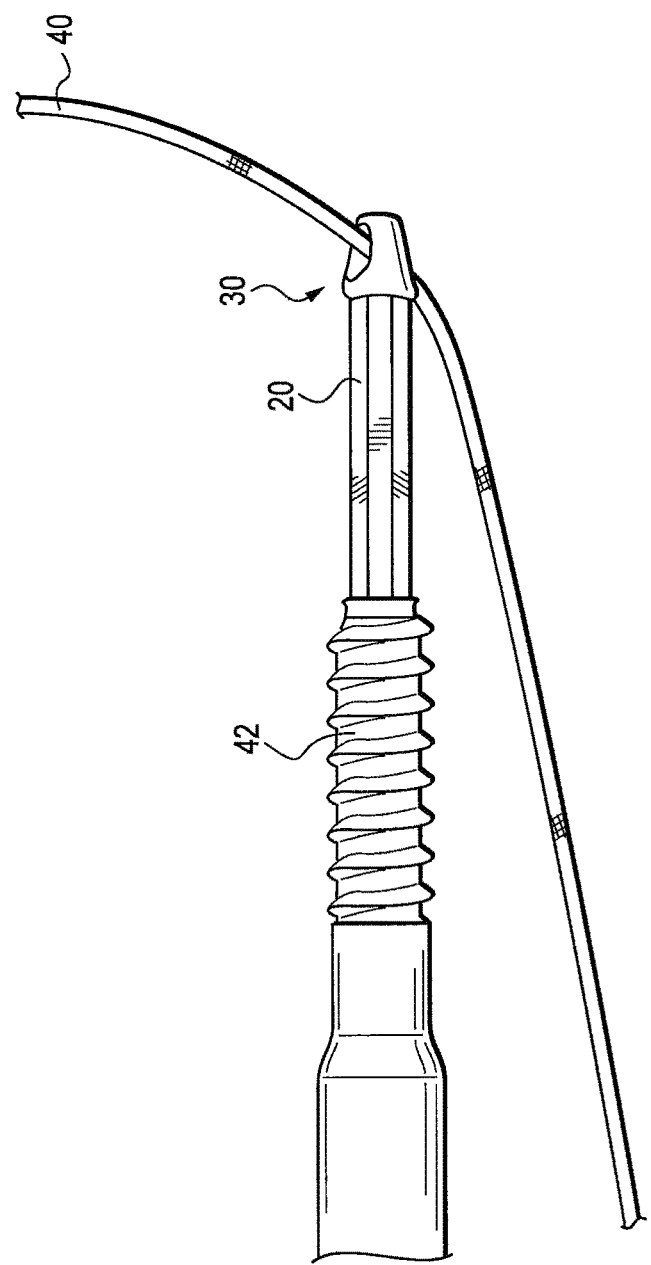
FIGS. 12 and 13 provide additional illustrations of the swivel anchor assembly of the present invention, and the swivel anchor inserted in a bone socket, respectively.
Figure 13:
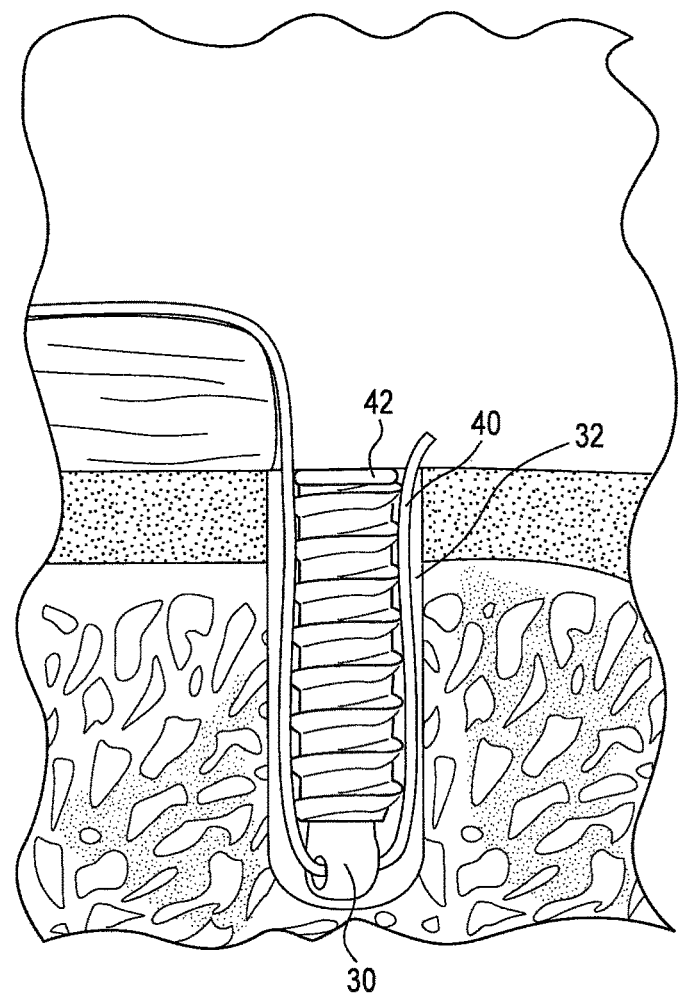

Referring to FIG. 5, one tail of suture tape 40 from each medial swivel anchor is retrieved and loaded through the eyelet of another swivel implant 30, and that implant is installed in then inserted into a preformed lateral bone socket. The tension of the suture tape 40 is adjusted if necessary. The swivel anchor driver is then rotated in clockwise direction as before to advance the screw 42 over the implant to complete insertion. This step is repeated in another lateral bone socket with the other tails of suture tape from each medial anchor. The tails of the suture tape 40 are then cut, one at a time, to complete the construct as shown in FIG. 6. The method is analogous to the method disclosed in U.S. Pat. No. 8,012,174, the entire disclosure of which is incorporated by reference herein. FIGS. 12 and 13 provide additional illustrations of the swivel anchor assembly and the anchor inserted in a bone socket, respectively.

Figure 10:
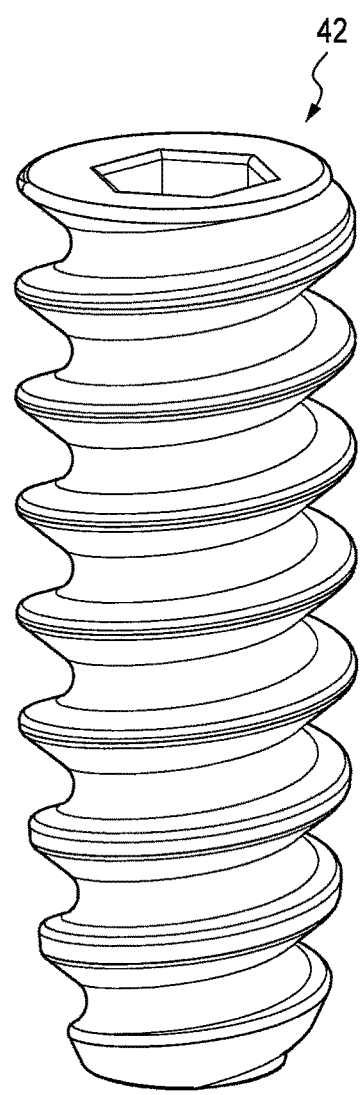
FIG. 10 is an enlarged view of the fixation device (cannulated screw) used in the present invention.
Figure 11A:
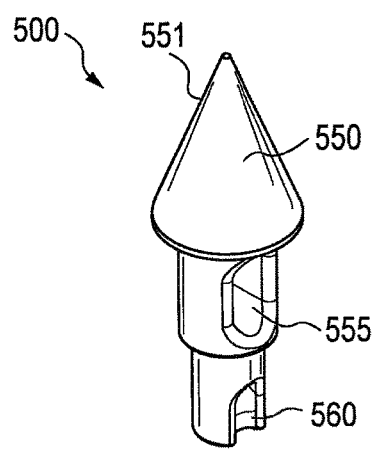
FIG. 11 illustrates various views of a swivel anchor with a metal tip which avoids the need to pre-drill a hole in bone.
Figure 11B:
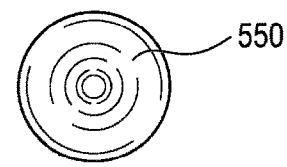
Figure 11C:
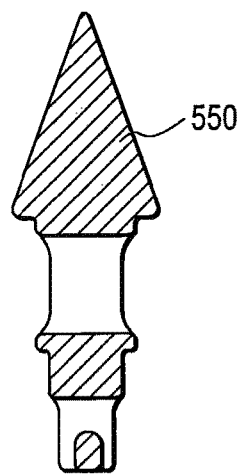
Figure 11D:
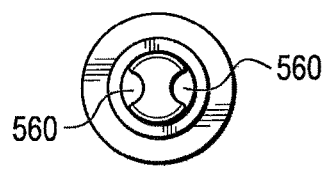
Figure 11E:
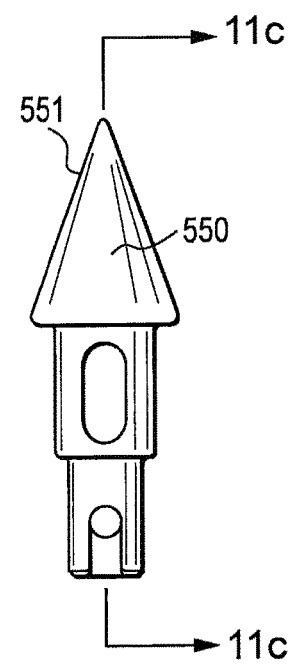

The swivel anchor and instruments of the present invention are now described in greater detail. As shown in FIGS. 7(a)-(f), a driver 68 is used to install the knotless fixation devices with a swiveling implant. Driver 68 features a thin cannulated rod 20 passing slidably and rotatably through a cannulated driver assembly. The tip of thin cannulated rod 20 is adapted to accept swivel anchor implant 30 within the cannulation at its tip, preferably via a snap fit. Cannulated rod 20 has a hexagonal outer surface for receiving anchor body (preferably a screw) 42 having a corresponding cannulation. FIG. 10 illustrates a detailed view of the cannulated screw 42.

Figure 7A:
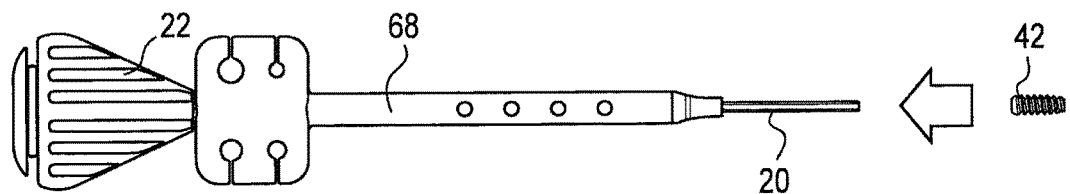
FIG. 7 illustrates various views of the driver assembly of the present invention.
Figure 7B:
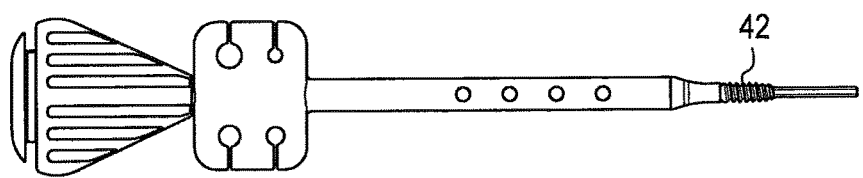
Figure 7C:
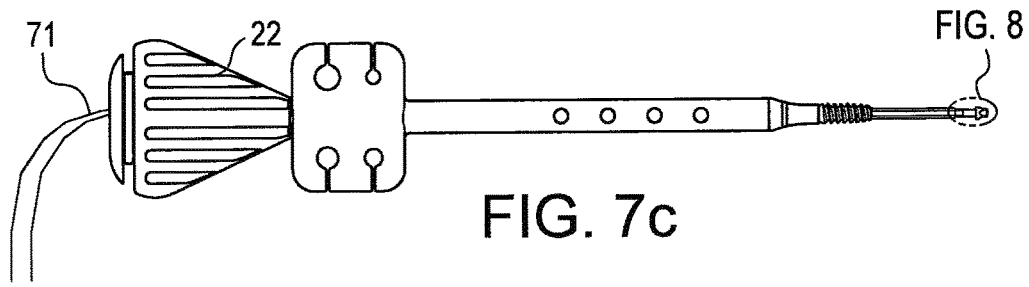
Figure 7D:
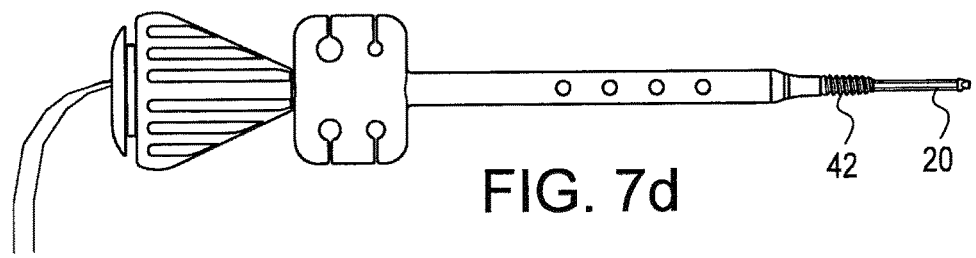
Figure 7E:
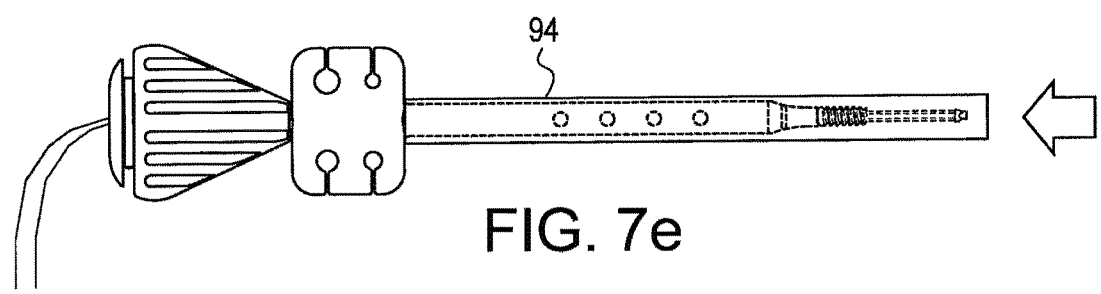
Figure 7F:
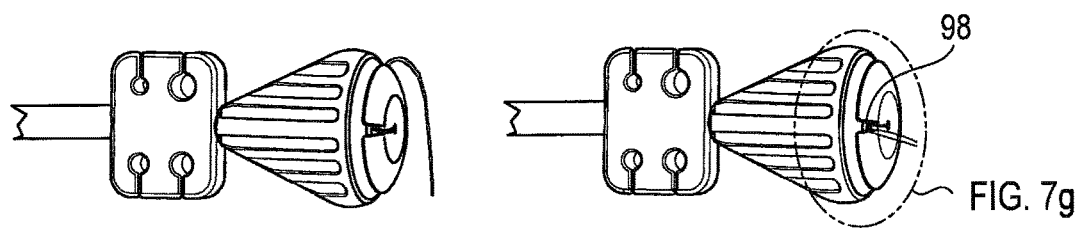
Figure 7G:
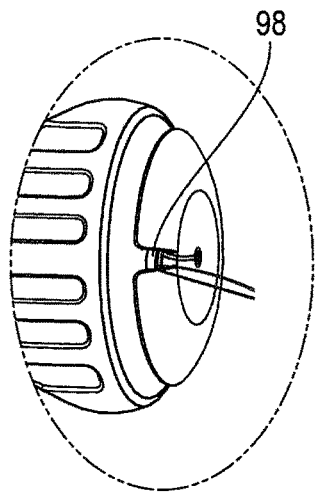
Figure 8:
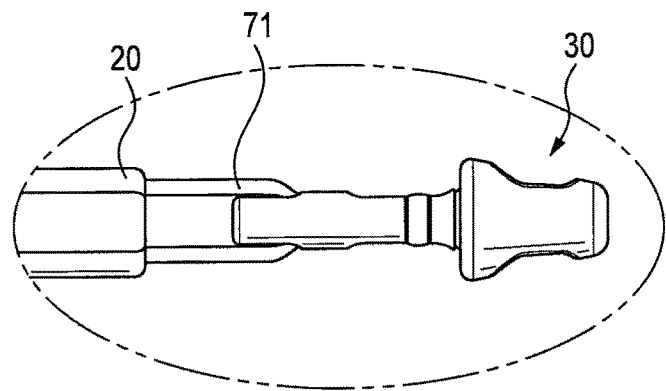
FIGS. 8 and 9 illustrate the swivel implant and traction suture.
Figure 9:
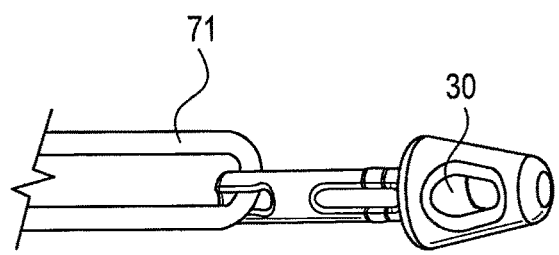

During installation of the knotless anchor having a swiveling implant 30, the screw 42 is first inserted onto cannulated rod 20 of the driver 68. As shown in FIGS. 7(a) and (b), screw 42 is loaded onto rod 20 and then fully seated on the shaft end of the driver. FIG. 7(c) illustrates the swivel anchor implant 30. As shown in FIGS. 8-9, traction sutures 71 extending from the proximal end of the swivel anchor implant 30 are threaded through the cannulation of the driver 68 (see also FIG. 7(c)). These traction sutures 71 prevent inadvertent separation of the implant 30 from the driver during insertion, but they can be used subsequently for additional tie-down of the tendon after the driver is removed. Subsequently, the swivel anchor implant 30 is seated on the driver tip and until advanced until it snaps onto place (FIG. 7(d)). A protective tube 94 (FIG. 7(e)) may be placed over the tip of the assembly for shipping purposes. The traction sutures 71 may be looped around the driver handle, as shown in FIGS. 7(f) and (g), and secured in a cleat 98 to prevent the implant 200 from becoming prematurely detached from the driver.

The knotless fixation device of the present invention advantageously minimizes or eliminates the need to tie knots. The use of such a swivel anchor also provides secure fixation of the suture construct—the secure suture construct results from the suture being pushed into a hole and held tightly by an anchors.

In the preferred embodiment of the present invention, as mentioned above, suture tape is used with the swivel anchor to fix tissue to bone. However, the swivel anchor of the present invention can be used with any type of flexible material or suture. In another preferred embodiment, an allograft or biological component may be used instead of suture or tape. The allograft or biological component may be comprised of tendon or pericardium, for example, which provides improved tissue repair. In yet additional embodiments, any combination of suture, suture tape, and allograft or biological component may be employed, depending on the characteristics of the specific surgical repair and/or as desired.

FIG. 11 illustrate a swivel implant 500 which is provided with a pointed metal tip to facilitate insertion of the implant without the need to pre-drill or pre-form a hole in the bone. The conical configuration of the most distal end pointed tip 550 allows the implant to undergo a self-punching operation, eliminating any need to pre-drill a hole in the bone. The conical configuration of the most distal end of the pointed tip implant 550 also provides suture fixation strength, as well as accelerated graft/tendon healing to bone. The pointed tip implant 550 may be detachable from the driver.

As illustrated in FIGS. 11(a)-(e), pointed tip implant 500 is provided with a metal tip 550 and an eyelet or aperture 555 for receiving suture or suture tape. Pointed tip implant 550 is also provided, at its most distal end, with a conical portion 551 which allows direct advancement of the implant (by simply tapping the device with a mallet, for example) without the formation of a pilot hole in bone. Preferably, the conical portion 551 of the implant is formed of titanium or titanium alloy. In a preferred embodiment, eyelet or aperture 555 is also formed of titanium or similar material, to withstand impaction forces during the graft fixation procedure.

Although the present invention has been described in relation to particular embodiments thereof, many other variations and modifications and other uses will become apparent to those skilled in the art. It is preferred, therefore, that the present invention be limited not by the specific disclosure herein.

What is claimed as new and desired to be protected by Letters Patent of the United States is:

1. A method of knotless tissue fixation comprising:
   providing a suture;
   securing the suture to tissue to be fixated;
   preloading a cannulated fixation device on a shaft of a driver;
   capturing the suture attached to the tissue with an implant, the implant being releasably attached at a distal end of the driver, the implant being configured to swivel relative to the cannulated fixation device;
   inserting the implant and the captured suture into bone; and
   anchoring the suture into the bone by rotating the driver to rotate and advance the cannulated fixation device while keeping the implant stationary, thereby securing the suture and providing tissue fixation without tying any knots in the suture.

2. The method of claim 1, wherein the cannulated fixation device is an interference screw.

3. The method of claim 1, further comprising the step of providing the implant at a distal end of the driver subsequent to the step of preloading the fixation device on the driver.

4. The method of claim 1, wherein the driver includes a cannulated rod passing slidably and rotatably through a cannulated driver assembly of the driver, the cannulated rod having a tip adapted to accept the implant, to allow the implant to be loaded onto the rod and be fully seated on an end of the shaft of the driver.

5. The method of claim 4, wherein the implant is releasably attached to the cannulated rod at the distal end of the driver by a snap fit.

6. The method of claim 5, wherein the cannulated rod has a hexagonal outer surface for receiving a corresponding inner surface of said cannulated fixation device.

7. The method of claim 5, wherein the cannulated fixation device is rotated and advanced by holding a thumb pad on a handle of the driver such that the implant swivels relative to the cannulated fixation device.

* * * * *